United States Patent [19]

Granberg

[11] Patent Number: 4,466,427

[45] Date of Patent: Aug. 21, 1984

[54] TRACTION DEVICE

[75] Inventor: Elof Granberg, San Rafael, Calif.

[73] Assignee: Granberg Pump & Meter Ltd., Richmond, Calif.

[21] Appl. No.: 308,005

[22] Filed: Oct. 2, 1981

Related U.S. Application Data

[63] Continuation-in-part of Ser. No. 182,551, Aug. 29, 1980.

[51] Int. Cl.[3] .......... A61F 5/00

[52] U.S. Cl. .......... 128/71; 128/75

[58] Field of Search .......... 128/71, 69, 70, 72-75; 254/199, 221; 64/29; 188/82.6

[56] References Cited

U.S. PATENT DOCUMENTS

| | | | |
|---|---|---|---|
| 951,515 | 3/1910 | Solsem . | |
| 1,605,578 | 11/1926 | Clark . | |
| 1,642,158 | 9/1927 | Kubista . | |
| 1,915,841 | 6/1933 | Warner . | |
| 2,773,499 | 12/1956 | Zur Neiden | 128/71 X |
| 2,798,481 | 7/1957 | Matthews | 128/71 |
| 2,861,565 | 11/1958 | Lapierre | 128/71 |
| 2,865,367 | 12/1958 | Sorenson | 128/71 |
| 3,238,936 | 3/1966 | Seidentrop | 128/71 |
| 3,276,444 | 10/1966 | Rice | 128/75 |
| 3,387,605 | 6/1968 | Schmidt | 128/71 |
| 3,420,229 | 1/1969 | Miller | 128/71 |
| 3,554,189 | 1/1971 | Hendrickson | 128/71 |
| 3,856,003 | 9/1973 | Pfluger | 128/75 |

FOREIGN PATENT DOCUMENTS

| | | |
|---|---|---|
| 92349 | 5/1962 | France . |
| 862277 | 3/1961 | United Kingdom . |

*Primary Examiner*—Stephen C. Pellegrino
*Attorney, Agent, or Firm*—Townsend and Townsend

[57] ABSTRACT

A portable traction device includes a frame which has an upper surface to support the individual to be subjected to traction. The frame has at least one mounting point at one end of the upper surface. At least one tension member emanates from the frame and has a free end passing through the mounting point and back toward the upper surface of the frame. The free end of the tension member is secured to the individual who is to be subjected to traction. A takeup mechanism for applying tension to the tension member is located on the frame. The takeup mechanism is activated, usually by the patient. The activation mechanism is adapted to disengage when the applied tension reaches a preselected value, while maintaining the preselected tension on the tension member.

5 Claims, 5 Drawing Figures

TRACTION DEVICE

This application is a continuation-in-part of co-pending prior application Ser. No. 182,551 of Elof Granberg for TRACTION DEVICE, filed Aug. 29, 1980.

BACKGROUND OF THE INVENTION

1. Field of the Invention

The present invention relates to traction devices, and in particular to a portable traction device which can be operated by the individual being subjected to traction.

In most modern hospitals, traction is applied to a patient using an electrically controlled winch system. The system includes a mechanism for setting the winch force needed to obtain the desired tension, and the system automatically maintains that tension on the patient.

While practical in most hospital environments, electric traction systems are impractical in many other situations where the application of traction is desired. For example, it is often desirable to provide traction in a home environment so that persons under traction, but otherwise not needing hospital attention, can receive treatment at home. In addition, it is often desirable to provide traction in an emergency at a location remote from a hospital, or to have traction equipment available in a hospital emergency room. In both of these latter situations, it is desirable to have traction equipment which is readily portable.

2. Description of the Prior Art

The patent literature contains a wide variety of traction devices, some of which are portable. Applicant is aware of the following patents which show traction devices: French Pat. No. 92,349; British Pat. No. 826,277; U.S. Pat. Nos. 951,515; 1,605,578; 1,642,158; 1,915,841; 2,798,481; 2,861,565; 3,276,444; 3,420,229; 3,554,189; and 3,856,003. French Pat. No. 92,349 illustrates a traction device operable by the patient. However, these devices in general are inefficient, cumbersome and complex, and do not satisfy modern medical standards as to the application of traction. Specifically, these devices do not provide precise control over the amount of traction applied, and they are not failsafe in the sense of preventing the application of excess forces which can harm the patient.

SUMMARY OF THE INVENTION

The present invention provides a traction device including a frame which has an upper surface to support the individual to be subjected to traction. The frame has at least one mounting point at one end of the upper surface. At least one tension member emanates from the frame and has a free end passing through the mounting point and back toward the upper surface of the frame. The free end of the tension member is secured to the individual who is to be subjected to traction. A takeup mechanism for applying tension to the tension member is mounted on the frame. The takeup mechanism is manually activated, usually by the patient. A tension-adjustment system is provided for automatically preventing the takeup mechanism from exceeding a preselected value of applied tension, while maintaining such preselected tension on the tension member until the patient releases it.

In the preferred embodiment of the present invention, the activating means comprises a manually-operated hydraulic pump mounted on the frame within reach of the patient. The takeup means comprises a hydraulic piston and cylinder assembly wherein the piston is driven by hydraulic pressure from the manually-operated pump and connected to the tension member, typically a flexible cable. Thus, the patient can increase the applied tension by continuing to operate the manual pump. To allow precise adjustment of the applied tension, a device (typically an adjustable relief valve) is provided to automatically relieve the pressure on the cylinder once a predetermined set point has been reached. Typically, the device will return the hydraulic fluid to the fluid reservoir. The range of operation of the pressure relief device is chosen so that the tension applied to the patient cannot exceed what is considered a safe level, even at its highest setting. A dump valve is provided to immediately relieve all pressure on the hydraulic cylinder when the patient desires to terminate treatment.

The present invention thus provides a very simple and convenient traction system which can easily be constructed so as to be portable. The entire system can be operated by the patient, thus facilitating its use in a home environment. Moreover, the device contains a failsale tension-adjustment system so that excess traction forces cannot be applied by mistake.

The novel features which are characteristic of the invention, as to organization and method of operation, together with further objects and advantages thereof will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

DESCRIPTION OF THE PREFERRED EMBODIMENT

Figure 1:
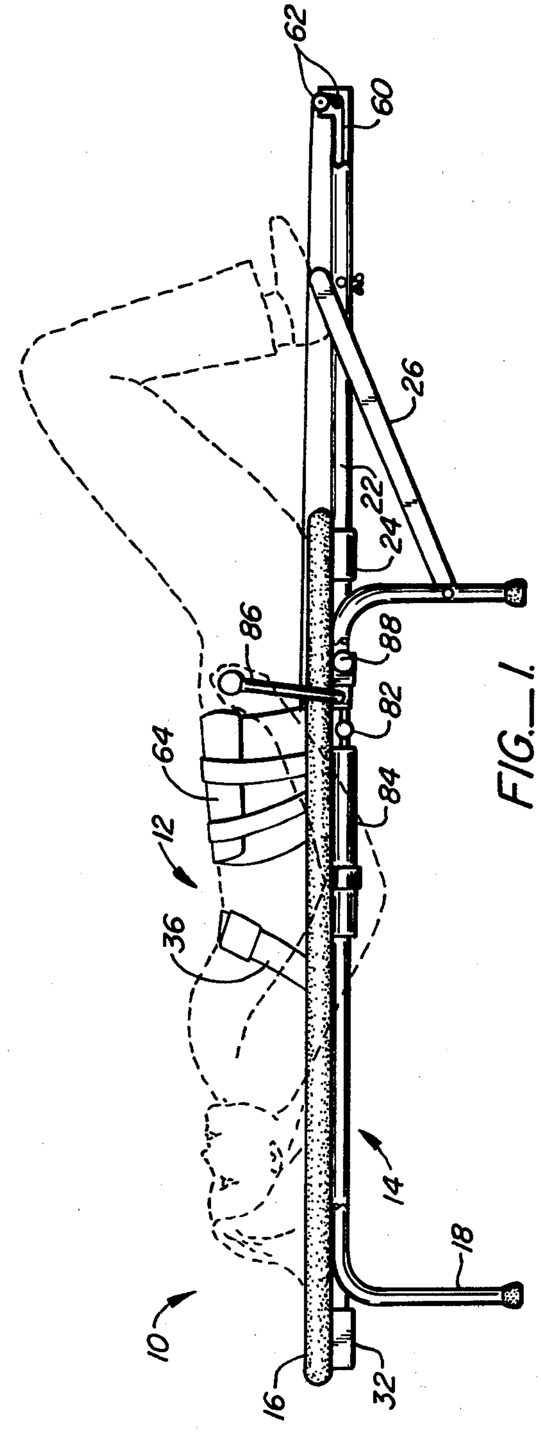
FIG. 1 is an elevational view of the device of the present invention, with portions broken away, being used in its pelvic traction mode.
Figure 3:
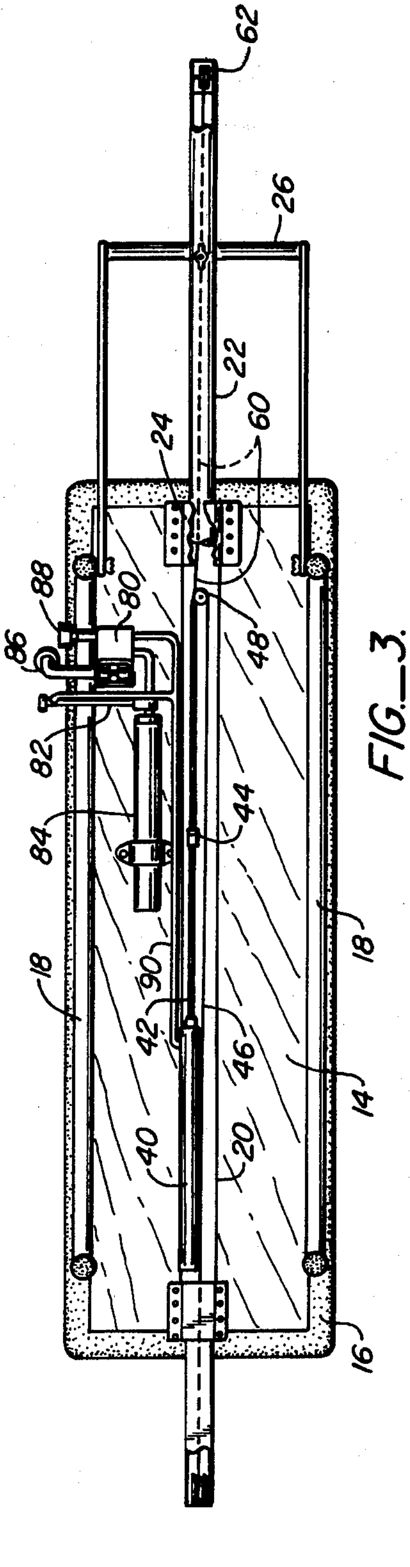
FIG. 3 is a bottom plan view of the traction device of the present invention, with portions broken away.
Figure 2:
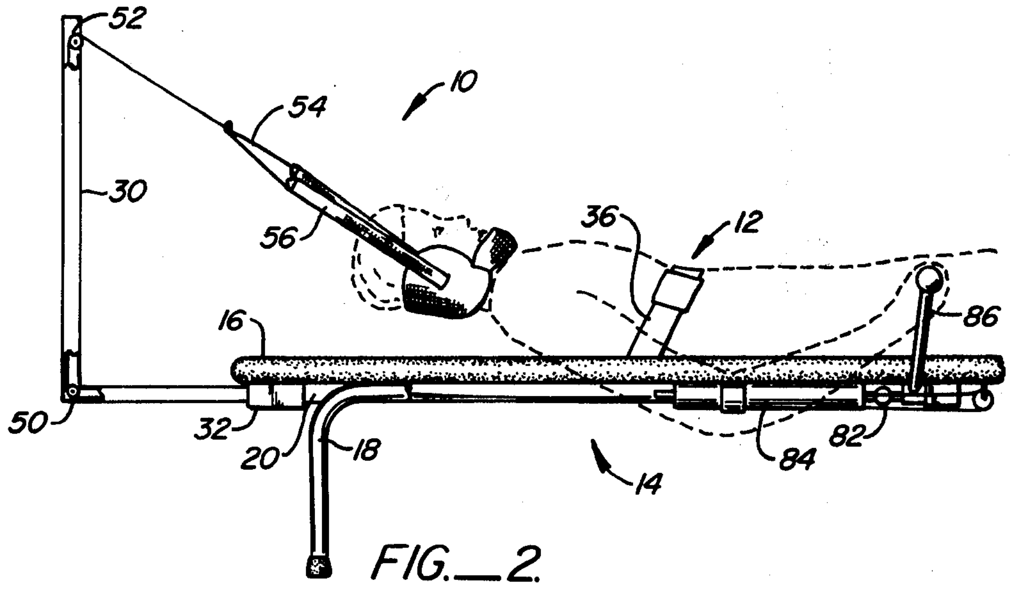
FIG. 2 is an elevational detail view of the traction device of the present invention, with portions broken away, being used in its cervical traction mode.

The traction device 10 of the present invention is illustrated generally in FIGS. 1–3. FIG. 1 illustrates a patient 12 being subjected to pelvic traction, while FIG. 2 illustrates the traction device 10 being used for cervical traction. Generally, a patient will be subjected only to one or the other kind of traction, but not to both simultaneously.

The traction device 10 includes a frame 14 which in turn comprises a padded board 16, folding legs 18 which may be retracted for transportation and storage, and a channel 20 secured axially along the middle of the underside of the board 16.

A pelvic traction post 22 is inserted into a bracket 24 at the foot of the frame 14 (to the right as viewed in FIG. 1). A foot bracket 26 is detachably secured at its lower end to legs 18 and at its upper end to the traction post 22. The foot bracket 26 acts both as a footrest for the patient during traction and as a structural member in helping support the traction post 22.

Referring now particularly to FIG. 2, a cervical traction post 30 is detachably inserted into a bracket 32 at the head of the frame 14 (to the left as viewed in FIGS. 1 and 2). The cervical traction bracket 30 is L-shaped and, when inserted in bracket 32, extends outward and upward from the frame 14. When using the traction device 10, the patient 12 lies on top of the board 16 and is held in place by a counter-traction belt 36 which is secured around the waist.

Referring now in particular to FIG. 3, a hydraulic cylinder 40 is mounted axially within the channel 20 on the underside of the frame 14. The cylinder 40 includes a rod 42 terminating in a block 44 at its distal end. As will be described more fully hereafter, the patient may manually actuate the cylinder 40 to draw the rod inward (to the left in FIG. 3) as a source of tension for the traction device 10.

Figure 4:
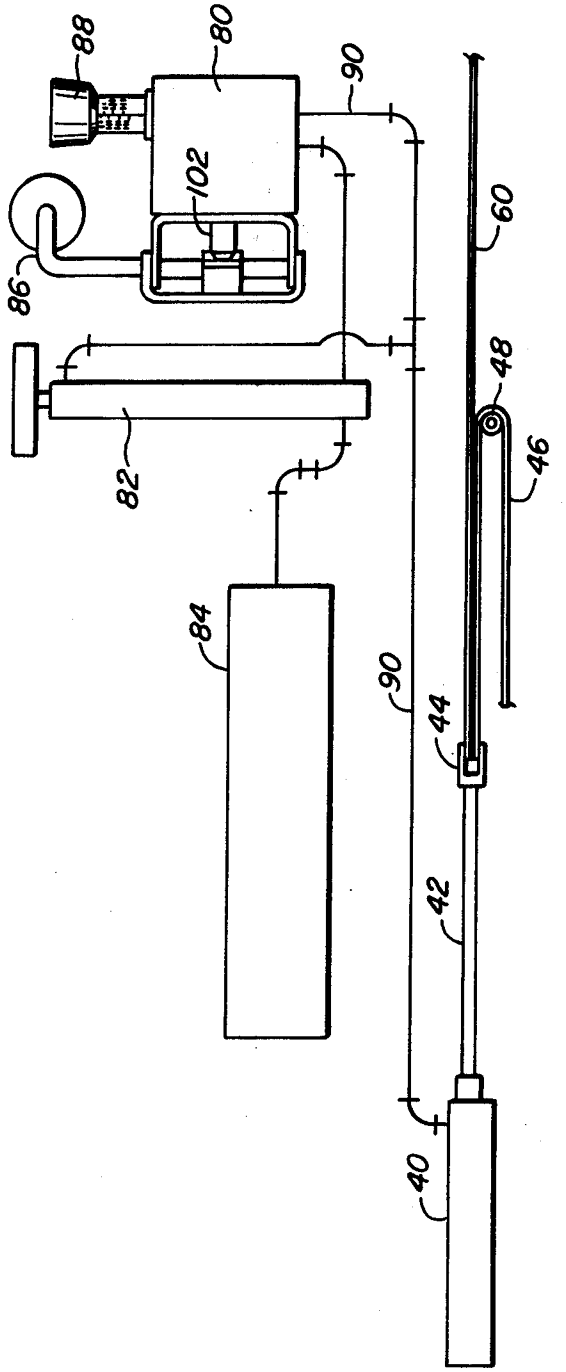
FIG. 4 is a schematic representation of the hydraulic system of the present invention.

A cervical traction cable 46 acts as a tension member and may be secured to the block 44 and drawn over an idler pulley 48, as illustrated in FIGS. 3 and 4. The cable 46 runs along channel 20 toward the head of frame 14 and into the cervical traction post 30 until reaching idler pulley 50 (FIG. 2) at the junction between the two legs thereof. Cable 46 then runs upward, around idler pulley 52 which defines a first mounting point and exits from post 30, as shown. The elevation of idler pulley 52 within the vertical leg of the cervical traction post 30 is adjustable to vary the angle at which the cervical traction is applied. The free end of the cable 46 connects to a spreader 54 which in turn is attached to a cervical halter 56 for the application of cervical traction to the patient 12.

In the case of pelvic traction, a pelvic traction cable 60 (similar to cervical traction cable 46 but having a different length) is attached at one end to block 44, as illustrated in FIGS. 3 and 4. The pelvic traction cable bypasses idler pulley 48 and extends to the foot of the frame 14 where it enters the hollow pelvic traction post 22. The cable 60 extends to the end of post 22 and reverses direction around idler pulleys 62 (FIG. 1) which defines a second mounting point. The cable 60 extends back toward (and generally underneath) the patient 12 where it is secured to a waist belt 64 which is wrapped around the patient's lower waist.

Using the cables 46,60 as described hereinabove, the single hydraulic cylinder 40 may be used selectively to apply either cervical or pelvic traction. The remaining systems of the present invention are common to both types of traction and are designed to apply a preselected pressure to the hydraulic cylinder, which, in turn, applies a corresponding tension to the patient 12.

Referring now to FIGS. 3 and 4, the hydraulic system of the present invention comprises the hydraulic cylinder 40, a pump and control block 80, a dump valve 82, and a hydraulic oil reservoir 84. The pump and control block 80 includes a pump handle 86 and a micrometer adjustment dial 88. Oil from the reservoir 84 enters the pump and control block 80 where the patient 12, or anyone else, may pump the oil up to a pressure which is set by adjustment of dial 88. Hydraulic line 90 connects the output of block 80 with the hydraulic cylinder 40 so that the piston therein realizes the full output pressure. The normally-closed dump valve 82 allows the user to relieve pressure from the cylinder to the oil reservoir when it is desired to terminate treatment.

Figure 5:
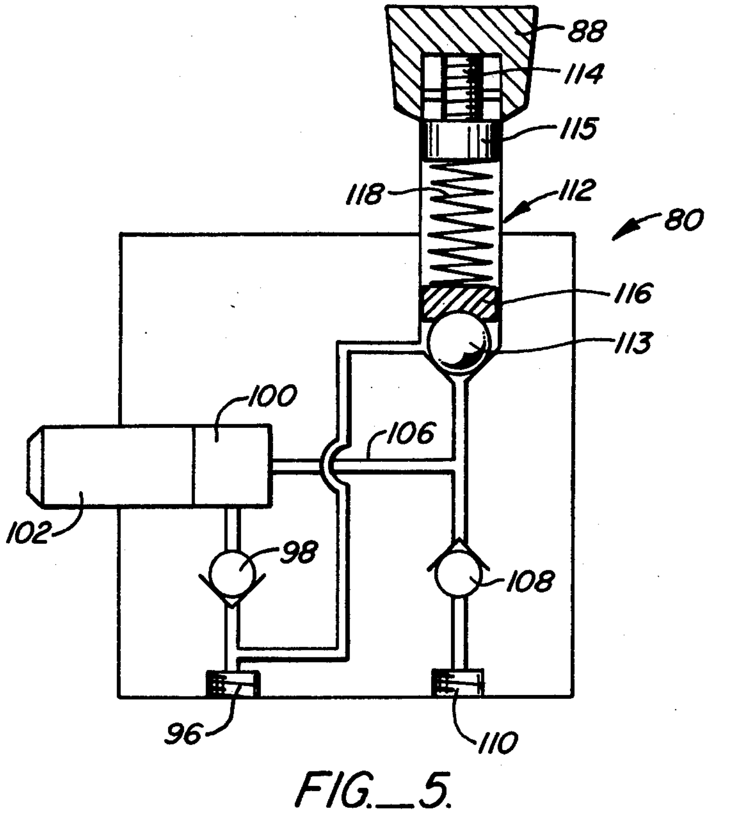
FIG. 5 is a schematic representation of the pump and control block of the present invention.

Referring now to FIG. 5, the pump and control block 80 includes an inlet port 96 which is connected to the oil reservoir 84. Oil is able to flow through port 96 and passed an inlet check valve 98 into a pump cylinder 100 formed integrally in the block 80. A pump piston 102 is operatively connected to the pump handle 86 (as best illustrated in FIG. 4) so that the user may reciprocate the piston to pressurize the oil and cylinder 100. The pressurized oil will pass outward through T-shaped passage 106 where it may flow past an outlet check valve 108, through an outlet port 110 and to hydraulic cylinder 40 (see FIG. 4). Alternatively, the oil in passage 106 may flow past the adjustable relief valve 112, depending on its set point and the pressure in the hydraulic line, as described hereinbelow.

The relief valve 112 is a spring-loaded check valve (defined by seating of ball 113 within the passage 106) where the tension on a spring 118 may be adjusted by the micrometer adjustment dial 88. Dial 88 is secured to a threaded shaft 114 which terminates in seal plug 115 within the valve housing. Thus, the seal plug 115 may be moved axially within the housing by rotating the adjustment dial 88. Such motion, in turn, adjusts the pressure applied on a ball pressure pad 116 by the spring 118. The ball 113 will remain seated in passage 106 until the pressure in the passage exceeds the force applied by spring 118 multiplied by the exposed area of the ball. When this occurs, the oil will flow past the ball 113 until the pressure is equalized. The adjustment dial 88 will typically be calibrated in pounds force applied by the cylinder 40 on the patient 12.

The pressure in the hydraulic cylinder 40 is a direct function of the tension on the associated cable 46 or 60. The tension on the cable (46 or 60) is, of course, determined by the traction force being experienced by the patient 12. Thus, until both the patient 12 and the traction cable are under tension, the cylinder 40 will not be pressurized. As soon as a cable begins to pull on the patient, however, the pressure in the cylinder 40 immediately begins to rise. The tension, and the pressure in the cylinder, will continue to rise as the user reciprocates handle 86 until the pressure in cylinder 40 exceeds the set point of the adjustable relief valve 112.

The relief valve 112 will be calibrated in pounds tension applied by the cylinder to the patient, typically in the range from 0 to 200 pounds. Such a range provides for both gentle cervical traction and the necessary heavier pull for pelvic traction. Once reached, the desired traction force will be maintained by the hydraulic system. After a time, however, the patient may relax and by so doing relieve pressure from the system. Should this occur, the patient need merely work the pump a little bit more to restore the desired pressure to the system. The patient need not worry that excess traction will be applied since the relief valve 112 prevents such overstressing.

The traction device 10 can be readily carried from one place to another until needed. Both pelvic traction post 22 and cervical traction post 30 may be removed from the frame 14 and secured to the underside thereof. Similarly, foot bracket 26 may be removed and stored on the underside of frame 14, while legs 18 fold up. Traction device 10 is then ready for transportation or storage.

While a preferred embodiment of the present invention has been illustrated in detail, it is apparent that modifications and adaptations of that embodiment will occur to those skilled in the art. However, it is to be expressly understood that such modifications and adaptations are within the spirit and scope of the present invention, as set forth in the following claims.

What is claimed is:

1. A traction device comprising:

a portable frame having an upper surface adapted to support an individual to be subjected to traction, and a pair of rods releasably engageable with the frame proximate the opposite ends of the upper surface and providing mounting points spaced from said upper surface;

a pair of tension members emanating from the frame and having free ends passing through the respective mounting points and back toward the upper surface of the frame;

a pelvic strap assembly attachable to the free end of one of the tension members and secured to the individual to provide pelvic traction, and a cervical halter attachable to the free end of the other tension member and secured to the individual to provide cervical traction;

a hydraulic cylinder mounted on the frame and capable of being secured to the tension members so that traction is applied to the individual when the cylinder is actuated;

a manually-operated pump mounted to the frame and fluidly connected to hydraulically actuate the cylinder;

means for adjustably limiting the maximum force applied to the cylinder by the pump while maintaining that maximum force until released; and means for releasing the force applied by the pump to the cylinder.

2. The traction device of claim 1, wherein the rod providing the mounting point for the tension member associated with the cervical halter has a vertical portion, and wherein the mounting point associated with cervical traction is movable along the vertical portion of said rod to vary the angle at which the cervical traction is applied.

3. The traction device of claim 1, further including a countertraction belt attachable to the patient below the rib cage and connected to the frame to provide countertraction during the application to pelvic traction.

4. The traction device of claim 1, wherein the means for adjustably limiting the maximum force applied is a relief valve having an adjustable set point and connected to relieve hydraulic pressure applied by the pump when it exceeds the set point.

5. The traction device of cliam 1, wherein the means for releasing the force applied by the pump is a valve connected to relieve hydraulic pressure in the cylinder.

* * * * *